United States Patent [19]

Pellerin et al.

[11] Patent Number: 5,024,091

[45] Date of Patent: Jun. 18, 1991

[54] NON-DESTRUCTIVE EVALUATION OF STRUCTURAL MEMBERS

[75] Inventors: Roy F. Pellerin, Pullman, Wash.; Robert J. Ross, Madison, Wis.

[73] Assignee: Washington State University Research Foundation, Inc., Pullman, Wash.

[21] Appl. No.: 365,218

[22] Filed: Jun. 12, 1989

Related U.S. Application Data

[63] Continuation-in-part of Ser. No. 843,717, Mar. 25, 1986, abandoned.

[51] Int. Cl.$^5$ ............................................. G01N 29/00
[52] U.S. Cl. .......................................... 73/597; 73/602
[58] Field of Search ................. 73/597, 588, 584, 582, 73/574, 618, 602

[56] References Cited

U.S. PATENT DOCUMENTS

| | | | |
|---|---|---|---|
| 2,439,130 | 4/1948 | Firestone | 73/597 |
| 3,087,138 | 4/1963 | Toulis | 73/597 |
| 3,423,991 | 7/1969 | Collins | 73/600 |
| 3,504,532 | 4/1970 | Muenow et al. | 73/597 |
| 3,512,400 | 5/1970 | Lynnworth | 73/597 |
| 3,513,690 | 5/1970 | Pellerin et al. | 73/594 |
| 3,858,437 | 7/1975 | Jarzynski et al. | 73/599 |
| 3,861,200 | 7/1975 | Dory | 73/599 |
| 3,888,108 | 6/1975 | Brands | 73/12 |
| 4,147,064 | 4/1979 | Bond | 73/597 |
| 4,163,393 | 8/1979 | Gutierrez et al. | 73/584 |
| 4,201,093 | 5/1980 | Logan | 73/618 |
| 4,338,820 | 7/1982 | Jassby | 73/597 |
| 4,361,154 | 11/1982 | Pratt Jr. | 128/660 |
| 4,420,210 | 9/1983 | Vandeberg | 73/12 |
| 4,481,820 | 11/1984 | Thomann | 73/597 |
| 4,492,117 | 7/1985 | Chubachi | 73/597 |

FOREIGN PATENT DOCUMENTS

918286  1/1973  Canada .

OTHER PUBLICATIONS

Kaiserlik, Joseph Henry, "Attenuation of Longitudinal Stress Waves as an Indicator of Lumber Strength", Washington State University, 1975.

(List continued on next page.)

Primary Examiner—Hezron E. Williams
Assistant Examiner—Louis M. Arana
Attorney, Agent, or Firm—Wells, St. John & Roberts

[57] ABSTRACT

Disclosed are testing apparatus and methods for estimating mechanical properties of nonhomogeneous materials, such as lumber and other wood materials and composite materials, particularly elongated slender members. The testing is appropriate for estimation of tensile and bending strength, tensile and bending moduli of elasticity and possibly other mechanical properties. The testing apparatus include a test specimen support which holds the specimen during testing in a manner which minimizes attenuation of the stress wave which is intentionally generated in the specimen to help predict the mechanical properties. The specimen supports also preferably include means for weighing the specimen which is combined with size information gathered through an optical scanning system thereby allowing the density to be obtained automatically. The specimens are impacted to produce a moving stress wave which is advantageously a longitudinal stress wave which moves longitudinally through the elongated slender members being reflected within the member preferably a number of times. The amplitude of the moving reflected stress wave is sensing with respect to time to allow the velocity and attenuation rate of the stress wave to be determined. The information is preferably communicated to a computer which automatically processes the sensed information and compares it to preprogrammed parameters which allow the accurate estimation of one or more of the predictable mechanical properties. The tested specimens are advantageously sorted according to the mechanical properties or appropriately marked to indicate the grade, strength or other appropriate measure of value of the specimen.

32 Claims, 11 Drawing Sheets

OTHER PUBLICATIONS

Kaiserlik, J. H., et al., "Stress Wave Attenuation as an Indicator of Lumber Strength", Forest Products Journal, vol. 27, No. 6, pp. 39–43.

Rose, J. L., "Ultrasonic Wave Propagation Principles in Composite Mat. Insp.", ASNDT *Materials Evaluation*, (43) (Apr. 1985).

Schoeer, R., "The Acoustic Impact Technique", *Non-Destructive Testing*, vol. 3, No. 3, (Jun. 1970).

Williams, Jr., J. H., et al., "Promising Quantitative NDE Techniques for Composite Materials", *Mat. Eval.*, 4-3 (Apr. 1985).

Hagemaier, D. J., et al., *Mat. Eval.*, vol. 43 ASNDT (Apr. 1985).

Matsuda, et al., "Automatic and Simultaneous Measurements of Ultrasonic Velocity and Attenuation Changes", *Rev. Sci. Instrum.*, 50(10) (Oct. 1979).

Ross, Robert J., et al., "NDE of Wood-Based Composites with Longitudinal Stress Waves", *Forest Products Journal*, vol. 38, No. 5, pp. 39-45 (1988).

Ross, Robert J., "Stress Wave Speed and Attenuation as Predictors of the Tensile and Flexural Properties of Wood-Based Particle Composites", Dissertation prepared for submission to Washington State University, Program in Engineering Science (1985).

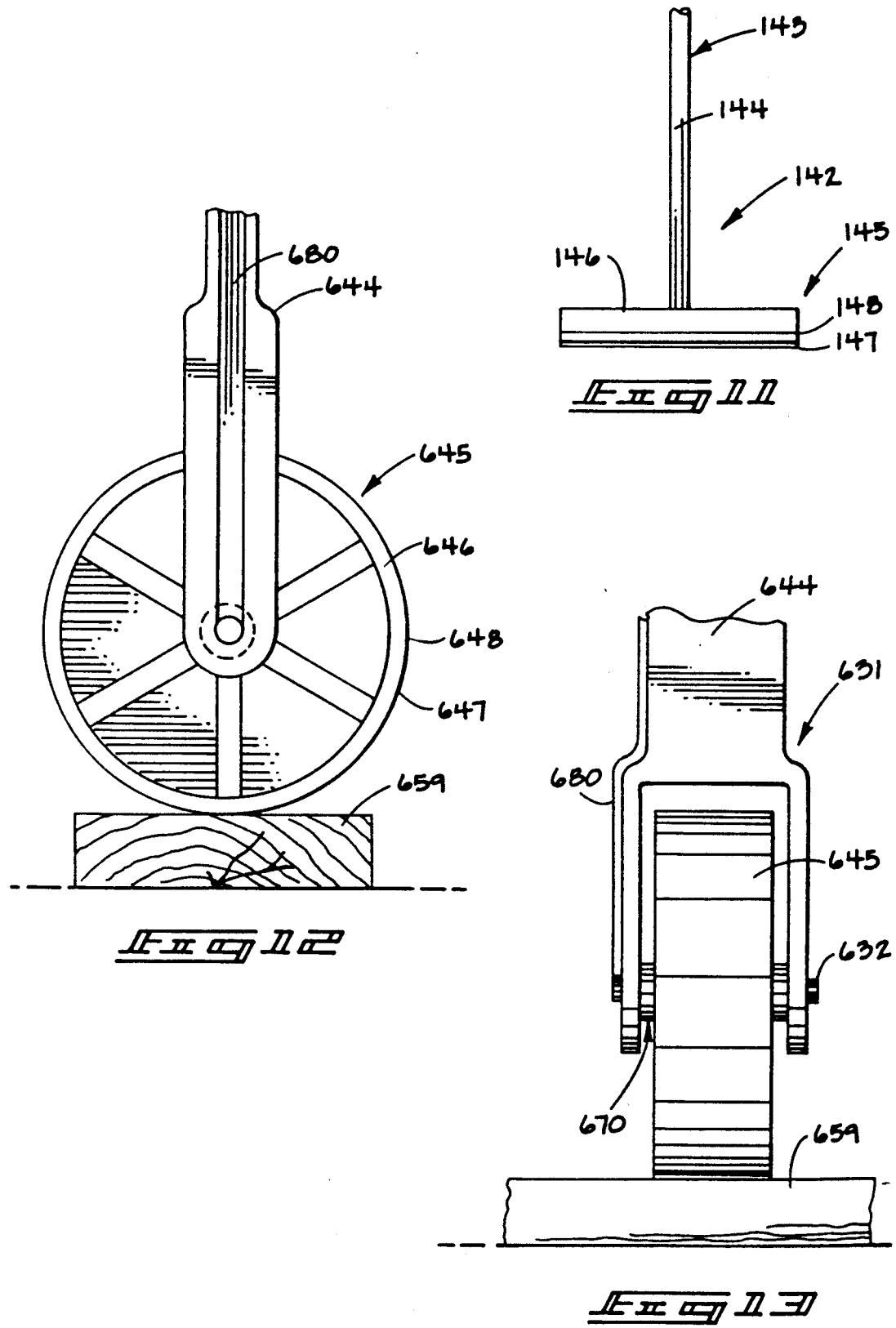

1

NON-DESTRUCTIVE EVALUATION OF STRUCTURAL MEMBERS

CROSS-REFERENCE TO RELATED APPLICATION

This is a continuation-in-part of copending allowed U.S. patent application Ser. No. 843,717, filed Mar. 25, 1986, entitled "Methods and Apparatus for Non-Destructing Evaluation of the Mechanical Properties of Composite Materials", now U.S. Pat. No. 4,838,085 issued Jun. 13, 1989, which is hereby incorporated by reference.

TECHNICAL FIELD

This invention relates to methods and apparatus for non-destructive evaluation of the mechanical properties of structural members, particularly structural members made of nonhomogeneous materials, such as woods and composite materials.

BACKGROUND OF THE INVENTION

There is increasing utilization of nonhomogeneous materials in engineered applications. Wooden lumber and wood-based composites are widely used in structural applications. Synthetic composite materials, such as fiber-resin composites also are now used in substantial amounts. However, such materials are not being utilized to their fullest potential because of difficulties in accurately determining the allowable working stresses to which structural members made of these materials should be subjected.

Much of the difficulty preventing full utilization arises because these nonhomogeneous materials do not exhibit uniform strength or elasticity properties from specimen to specimen. Wood materials by nature include numerous knots, separations, grain variations, and inherent differences in the strength of the wooden fiber matrix. Composite materials suffer significant variations in bonding between reinforcing fibers and the resin filler or other matrix or binders. Wood-based composites such as particle boards, wafer boards, plywoods, glued laminated beams and others combine some of the difficulties of both. Accordingly, it has been impossible to provide strength or elasticity grading information which allows for full use of relatively stronger members contained within a group or class of structural members having significant variations in strength, elasticity or other mechanical properties. More typically, the allowable working strength and elasticity properties have been predominantly determined by the weakest members in a class.

Also of concern is the increasingly widespread use of lumber in structural applications in which the lumber is stressed in tension, as compared to bending or compression. For example, chords of trusses, wooden I-beams, and tensile laminae of glued laminated timbers are primarily used under conditions were the primary potential failure mode is in tension. This has generated serious questions concerning the validity of assigned strength and elasticity values which have traditionally been almost exclusively based on strength testing in bending or flexure. Most of the allowable working stresses assigned to lumber have been derived from bending tests wherein the strengths are initially determined by bending the members to failure. This basic bending failure strength information is then extrapolated through theoretical analysis and assumptions to predict corresponding strength and elasticity properties in tension. Because of the relatively large factors of safety incorporated in allowable working stress values this lack of relationship to actual tensile testing has in most cases not caused disastrous results. However, the more efficient utilization of wooden members strongly suggests the need to have more accurate engineering models and information for designing members subjected to different types of stress.

The increased utilization of lumber in tension applications is also rendered more problematic because the tensile properties of lumber are more difficult to predict than are bending properties when using the lumber grading systems, visual grading systems and machine stress rated system currently used in lumber production. These current grading systems are unable to assess tensile properties with sufficient precision due to inefficiencies in the relationships between the detected flaws, proof testing techniques, or force-deflection response characteristics used in such systems and their appropriateness for predicting tensile properties. Such prior grading systems typically sort relatively high strength pieces into grades of lower strength and value because they are unable to identify the higher tensile strength members. The discrimination criteria used thus under-utilizes a majority of the pieces tested.

Current lumber grading technologies also suffer from limitations associated with their inability to grade green lumber or lumber otherwise having a moisture content greater than 19%. This limitation leads to vast amounts of wasted energy because lumber which is intended for use in special applications is dried prior to grading for strength. This leads to costly drying of a substantial amount of lumber which is not of sufficient strength for such higher uses. If such relatively weak lumber could be graded out prior to drying then substantial economic benefits and energy savings could be realized.

Wooden and composite materials are not being utilized to their fullest potential and great economic losses are associated with not selectively using stronger and better members where they have the greatest value. As the value of these materials increases the need becomes more acute to properly grade nonhomogeneous structural members based upon their particular strength and elasticity capabilities.

BRIEF DESCRIPTION OF THE DRAWINGS

Preferred embodiments of the invention are illustrated in the accompanying drawings which are briefly described below.

FIG. 11 is a detail side elevational view of the sensor head used in the testing apparatus of FIG. 1.

FIG. 12 is a detail front elevational view of an alternative novel sensor head which can be used in testing apparatus according to this invention.

FIG. 13 is a detail side elevational view showing the sensor head of FIG. 12.

DETAILED DESCRIPTION OF THE PREFERRED EMBODIMENTS

The following disclosure of the invention is submitted in furtherance of the constitutional purpose of the Patent Laws "to promote the progress of science and useful arts" (Article 1, Section 8).

Figure 1:
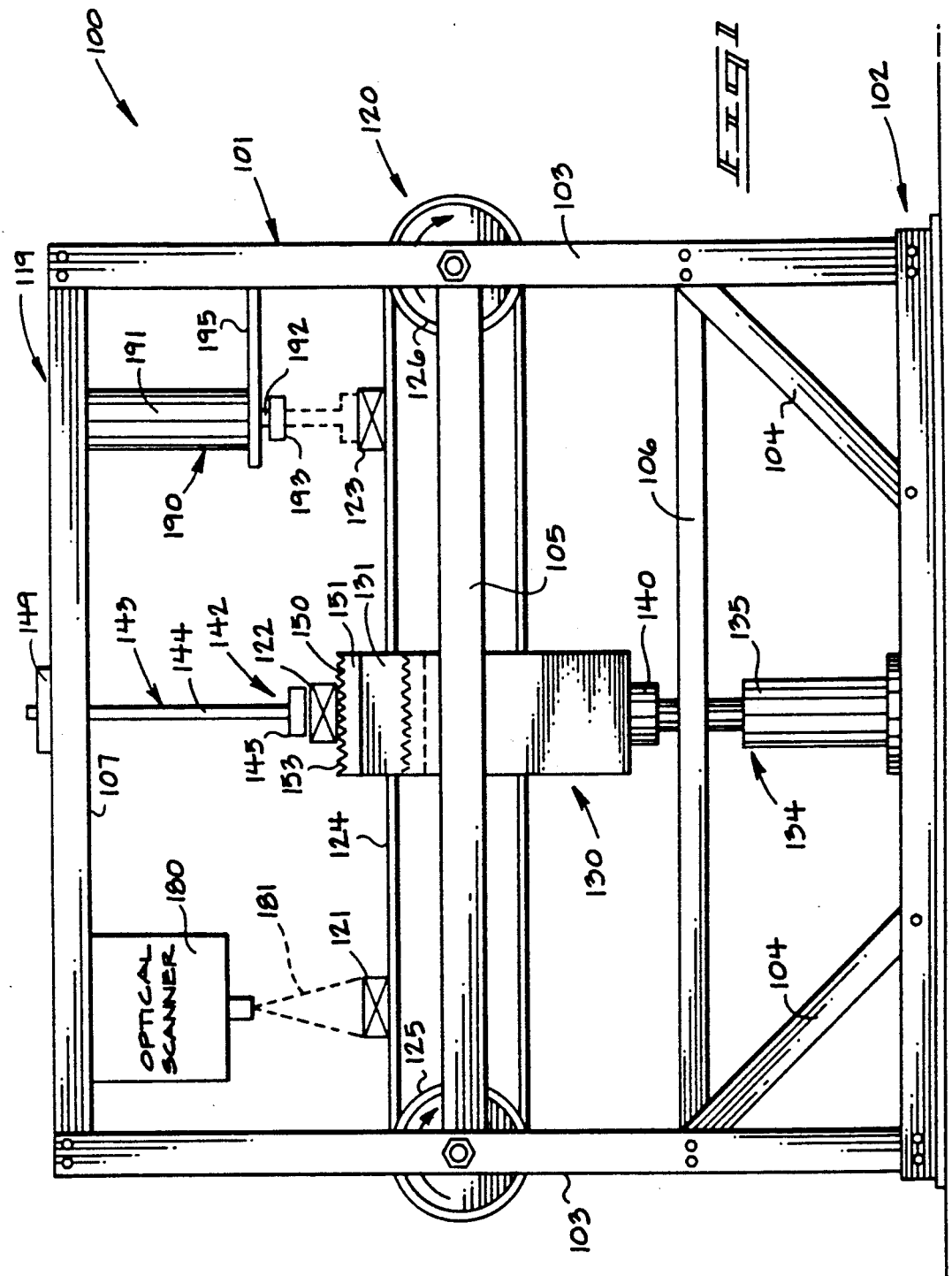
FIG. 1 is a front elevational view of a preferred testing apparatus according to this invention.
Figure 2:
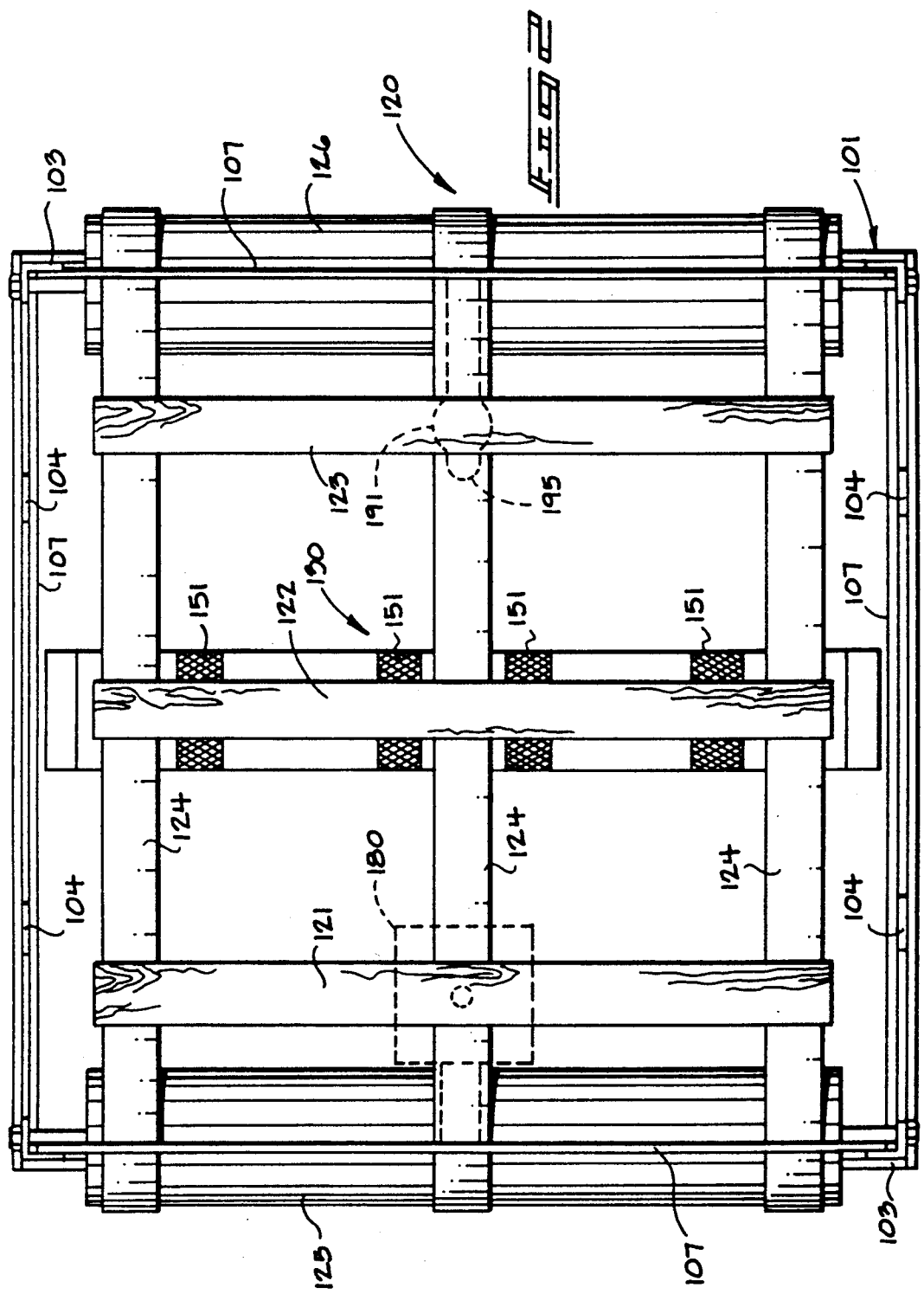
FIG. 2 is a top plan view of the embodiment shown in FIG. 1.

FIGS. 1 and 2 show a preferred testing apparatus 100 according to the present invention. Testing apparatus 100 includes a frame 101 having a base 102 and upright columns 103. Base 102 and columns 103 are connected by braces 104. Horizontal bars 105 and 106 extend between the upright columns. A superstructure is provided using the upright columns and upper horizontal bars 107.

Frame 101 supports a specimen conveyor 120 for moving test specimens 121–123 along to different stages of processing during the testing. Conveyor 120 preferably includes a plurality of conveyor belts 124 which support the structural member specimens being tested. The conveyor belts are mounted in a circuitous arrangement about a roller set, which as shown includes rollers 125 and 126. Rollers 125 and 126 are rotatably supported upon the frame 101, preferably at the elevation of horizontal bars 105. The conveyor rollers 125 and 126 can be driven using a motor and pulleys (not shown), internally mounted motor assembly (not shown), or in any other suitable fashion. The motor or other conveyor driver 129 (see FIG. 9) used to rotate rollers 125 and 126 is preferably adapted for relatively precise positional control to allow positioning of the test specimens with accuracy.

The plurality of conveyor belts 124 allow a plurality of test specimen support assemblies 130 to be positioned at both ends and a desired number of intermediate support positions along the length of the specimens. As shown there are four support extensions 131 which are controllably extendible from retracted positions, such as partially shown in phantom in FIG. 1, and extended positions, such as shown in solid lines in FIG. 1. The support extensions are mounted upon one or more test specimen support actuators 134 for controllably moving the support extensions 131 upwardly to allow total support of the structural member 122 in the extended position. The actuators 134 are contracted to move the support extensions downwardly into a retracted position to bring the structural member test specimen 122 down onto the conveyor belts 124 for further processing by the testing apparatus 100.

As shown, there is one specimen support assembly actuator 134 which comprises a hydraulic or pneumatic ram assembly 135. The ram assembly 135 is preferably mounted to the base 102. The support extensions 131 are preferably joined together in a unified array by specimen support cross members to provide uniform lifting action for the structural member specimen 122. Multiple and independent construction and operation of the specimen support assembly actuators and supports is also possible.

The upper end of the ram assembly 135 is preferably mounted with a load cell assembly 140. Load cell 140 is preferably selected to provide an electronic output signal indicative of the weight carried by the actuator 134. The inclusion of load cell assembly 140 allows the structural member test specimens, such as specimen 122 to be automatically weighed as it is lifted into a testing position, as shown in FIG. 1. The output signal from the load cell 140 is communicated to a computer or other similar computational device 400 (FIG. 9) which is described in greater detail hereinafter. Load cell 140 can be selected from a variety of well-known load or weigh cells having the desired weight carrying capacity and sufficient durability to withstand the continuous cycling of testing apparatus 100. The load cell 140 comprises one preferred form of specimen weighing means, other alternative types will also be possible.

The structural member support assemblies 130 are preferably adapted to provide a particularly advantageous type of specimen contacting surface or surfaces 150. Structural member support surface 150 is preferably formed to yield to transverse shear stresses which are developed in the test specimen when a moving stress wave is induced therein as explained more fully hereinafter. By reducing the mechanical coupling between the specimen support surfaces and the specimen, the transverse shear stresses are not suppressed and the moving stress wave is not artificially dampened. Dampening of the moving stress wave is disadvantageous because it is a key measurement quantity used in the apparatus and methods of this invention to predict mechanical properties of the structural member test specimens being analyzed. As shown, the specimen support surface 150 advantageously comprises a flexible and resilient layer 151. Specimen support layer 151 advantageously has a plurality of spaced projections 153 forming the upper support surface 150 into an undulating shape with discrete spaced contact areas formed on the distal ends of the projections 153. This structure allows the moving stress wave in the elongated structural member 122 to tranverse back and forth within the member many times due to the low attenuation from mechanical coupling between the support and the specimen.

Figure 9:
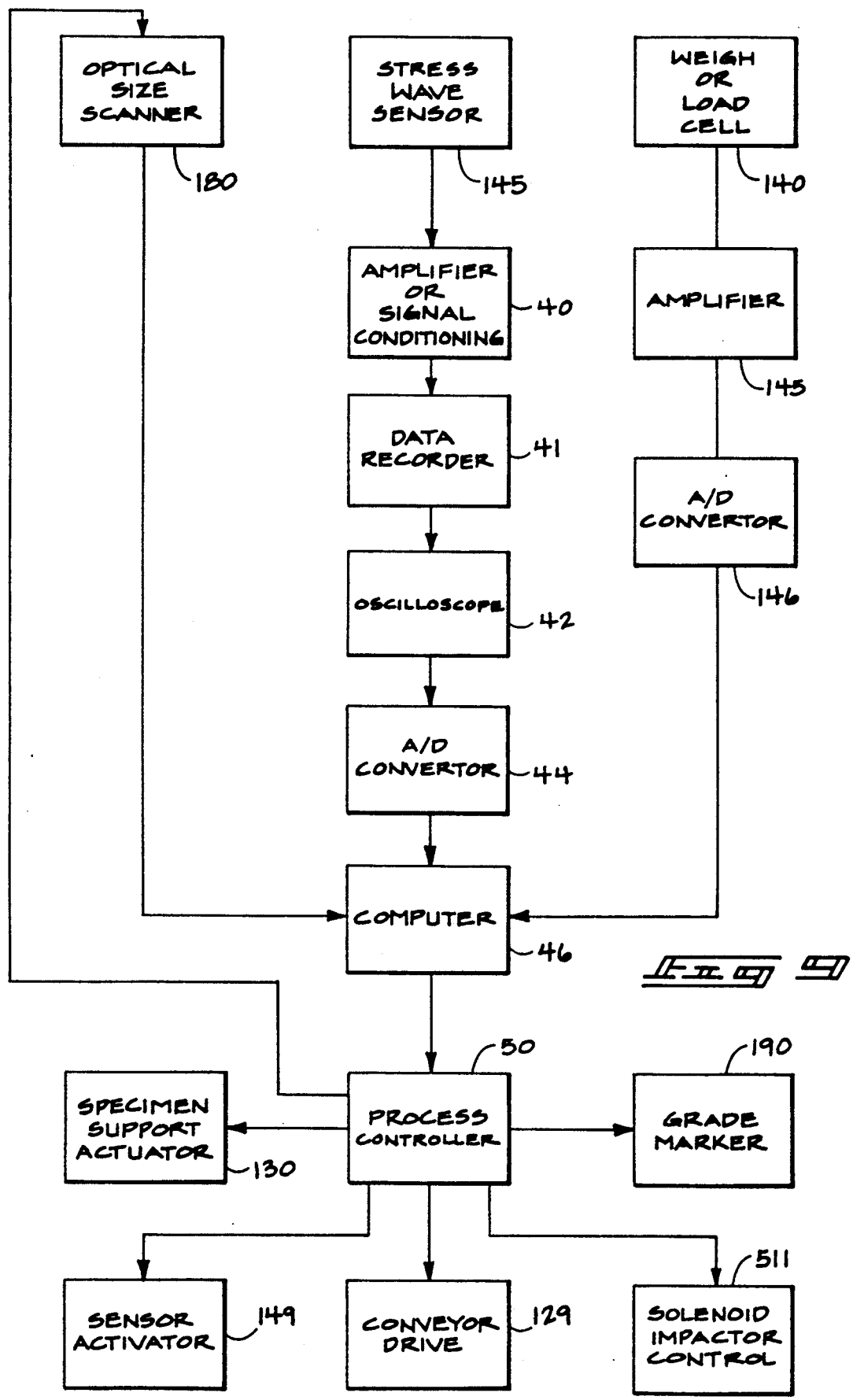
FIG. 9 is a schematic diagram showing a preferred form of control system useful in apparatus made in accordance with this invention.
Figure 10:
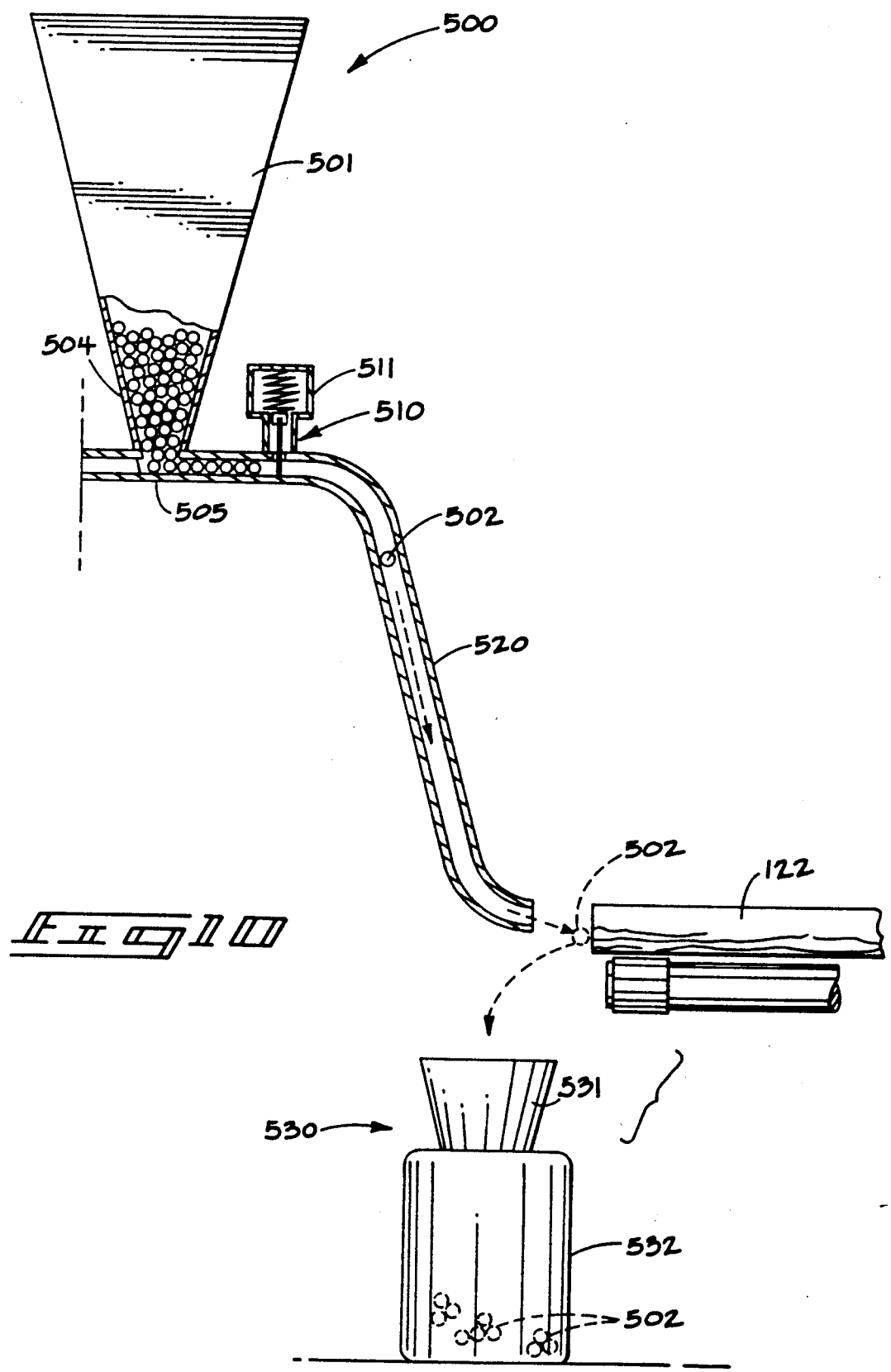
FIG. 10 is a diagrammatic sectional view showing a preferred impactor subassembly which can be used in the embodiments described hereinabove.

A moving stress wave can advantageously be generated in the supported test specimen 122 using a variety of stress wave inducers. FIG. 10 shows a preferred impactive stress wave inducer subsystem 500 which can be used in the testing apparatus 100 and the other testing apparatus described herein. The subsystem 500 is located adjacent the end of specimen 122 or otherwise as is desired to induce a moving, preferably longitudinal, stress wave therein. Subsystem 500 includes a supply container 501 which is advantageously shaped as a hopper, and is used to hold a supply of impactive projectiles 502. The impactive projectiles 502 are preferably hard balls, such as made from a metal. The hopper 501 tapers to a outfeed 504 which supplies a collimator 505 which arranges the outflow of projectiles into a single file from whence they are intermittently released using a slide gate 510. The slide gate 510 is preferably actuated by a solenoid 511 which can be automatically controlled by the computer 46 or process controller 50 (FIG. 9).

The impactor subsystem 500 operates by controllably releasing the projectiles which roll down a directive conduit 520. The conduit is arranged to provide a particular range or amount of energy in the projectile which the projectile impacts the specimen. The gravity-determined control of the projectile energy is very helpful in providing a relatively uniform stress wave signal energy which can thus be fully monitored for an expected signal strength. The impacted projectiles bounce or ricochet off the specimen, preferably at the end, thus imparting energy to the specimen and generating the stress wave therein. The ricocheted projectiles are received in an impacted projectile receptacle 530 which advantageously includes a funnel top 531 and reservoir 532. The projectiles 502 can periodically be transferred from the reservoir 532 to the supply container 501 either manually or using an automatic ball conveyor (not shown).

FIG. 1 further shows that testing apparatus 100 also advantageously includes a stress wave sensor assembly 142. The stress wave sensor assembly is mounted upon the end of a retractable and extendible sensor mounting 143. The mounting preferably includes a linear actuator which allows the sensor assembly and support bar 144 to rest simply under the force of gravity to provide a reliable amount of downward pressure on the specimen 122 by sensor head 145. One preferred sensor head construction is shown in greater detail in FIG. 11. The sensor head 145 includes a backpiece 146 which is connected to bar 144 and provides a desired mass for the total unit. The downward, specimen contacting face is formed by a thin piezoelectric film 147. A suitable film is Kynar brand by Pennwalt Corp. of Valley Forge, PA., type LDT1-028K. Others are also potentially useful. The piezoelectric sensor film is supported by a padded or resilient layer 148 which can be made of various foam rubbers or similar relatively soft elastomeric or other resilient material. The layers are preferably bonded together using a suitable adhesive. The piezoelectric film has two electrodes or connections which are connected to suitable electrical conductors (not shown) for transmitting or communicating the sensor signal to related signal processing equipment such as amplifier 40 (FIG. 9).

The superstructure of frame 101 is advantageously used to support an automated means for determining the size or volume of the structural members being tested. FIG. 1 shows an optical scanner 180 which is mounted to the frame or other suitable arrangement to scan an optical beam 181 down upon the conveyor 120 and determine with a high degree of accuracy the size and volume of the particular specimen 121 being tested. Depending on the type of scanner used the thickness of the lumber or other material being tested may be input by the operator rather than automatically read from the specimen. Optical scanner 180 can be selected from a number of commercially available scanning systems used in the lumber production industry for various monitoring and size determining functions. Laser scanners are known in the art of lumber processing equipment and such scanners or other equivalents are useful as a size or volume determining means in apparatus made in accordance with this invention. The information obtained by optical scanner 180 is communicated to the computer 400 for storage and association with the measured data obtained during testing by apparatus 100.

FIG. 1 also shows that testing apparatus 100 preferably includes a grade marker 190. Grade marker 190 can be of a variety of types. As shown, grade marker 190 comprises a pneumatic ram 191 having an extendible piston 192. Piston 192 mounts a marker head 193 which bears directly onto the tested specimen 123 to provide an embossed mark indicative of the strength, elasticity or other mechanical property predicted by testing apparatus 100 from direct testing and analysis of the specimen. The grade marker 190 can be supported on frame 101, such as by using a transverse support bar 119 at the upper end of the ram, and by lower restraint bar 195, or using other suitable means. The testing apparatus 100 can be provided with one or more such grade markers as desired depending upon the number of grades being output from the device. Each of multiple grade markers can be independently controlled by computer 46 or process controller 50 via a suitable pneumatic control valve (not shown) to mark the various grade markings on the specimens. Inked grade markers and other appropriate indicia of grade type can alternatively be used.

FIG. 9 shows a preferred automatic control system advantageously used in the testing machine 100 described above. The automated control system includes the stress wave sensor 145 which produces an electronic stress wave sensor output signal. The stress wave sensor output signal is communicated to a signal amplifier or other suitable signal conditioning circuitry 40 of suitable design for the particular sensor or sensors employed in the machines built according to this invention. In some cases such circuitry may not be needed if the output signal from the sensor is sufficiently strong and clear. The amplified stress wave sensor signal is advantageously communicated to a data recorded 41 which can be portable if a portable system is used, or part of computer 46 or arranged otherwise as known in the art. An oscilloscope 42 can be included for display purposes. Alternatively, the oscilloscope can be omitted and the conditioned or suitable unconditioned sensor signal can be communicated directly to an analog-to-digital converter 44 which provides a digital stress wave sensor signal. The digital stress wave sensor signal or signals are preferably communicated to a general purpose computer 46 which is suitably programmed for data acquisition. The computer 46 also receives information from the optical size scanner system 180 in the form of a digital representation of the perimeter of the specimen scanned by the optical scanner, or in other suitable mathematical representation. Such information is typically already in digital form and conversion is not needed as in the case of the analog stress wave sensor signal. The computer further receives information indicating the weight of the specimen from the load cells 140. The load cells produce an analog specimen weight signal which is amplified by a suitable amplifier 145 and converted into digital form by analog-to-digital converter 146. The digital weight signal is communicated to the computer 46 for analysis with the size information to produce an indication or measure of the specimen density.

The computer 44 also performs analysis as described hereinafter to estimate one or more mechanical properties of the specimen being tested. The results of such analysis is used to either directly or indirectly control the grade marker 190. In lieu of grade marker 190 it is also possible to store information about the grade of each specimen, to track the tested specimen, and to sort the tested specimen into appropriate grade lots using suitable sorting machinery, such as shown below in connection with FIG. 7. The grade marker can also be controlled by process controller 50 which can be either a subsystem of computer 46 or a discrete control module.

The process controller is also preferably used to control the conveyor drive motor 129 which determines the operation of specimen conveyor 120. The computer and/or process controller also preferably outputs a suitable optical scanner control signal to coordinate the operation of the optical size scanner 180 with the remainder of the testing apparatus. Process controller 50 further controls the operation of the specimen support actuators 130 via one or more suitable solenoid actuated hydraulic or pneumatic control valve (not shown) thereby allowing the specimen 122 to be raised into the tested position and retracted for further conveyance. The process controller also preferably controls the operation of the sensor actuator 149 and the impactor slide gate solenoid 511. Thus the control system provides complete automated control of the testing apparatus 100.

The operation of the testing apparatus 100 will now be more fully described. Elongated lumber specimens such as specimens 121—123 are fed to the testing apparatus 100 from associate infeed equipment not shown. The general flow of the product being tested is from left to right as shown in FIG. 1. The computer 46 or process controller 50 controls the conveyor operation and moves the specimen 121 into position under the optical scanner 180. At this first station the optical scanner determines the size of the specimen being tested by scanning a laser beam over the specimen and detecting the laser reflected from the specimen. At the same time that specimen 121 is being optically scanned the specimen 122 which has already been scanned, is lifted from the conveyor 120. Specimen 122 is lifted from the conveyor by controlling the hydraulic or pneumatic control valves (not shown) which control the operation of the specimen support actuation ram 135. The ram is controlled to extend and lift the specimen 122 into the elevated and removed position away from the conveyor surface. As the specimen supports lift the specimen 122 the weight of the specimen is carried through the load cells 140 and the change in load cell output signal indicates the weight of the specimen being tested. This information is analyzed by computer 46 along with the size information from the optical scanner 180 to produce a measure of the average density of the specimen 122 being tested.

After the specimen 122 has been lifted into the testing position shown in FIG. 1, the stress wave sensor 145 is lowered by the linear actuator 149 into position contacting the specimen to detect the stress wave which is to be induced in the specimen. The stress wave inducer or impactor ball 502 is then released to strike the end of the specimen 122. The impact causes a freely moving or self-propagating stress wave to develop within the specimen which is primarily a longitudinal compressional wave as the initial stress wave traverses down the specimen from the point of impact. The stress wave sensor detects magnitude, sense and time of the passage of the stress wave and communicates this information to the computer 46. At the end of the specimen opposite to the impactor the longitudinal compression wave reflect off of the end surfaces of the specimen and is transformed into a moving longitudinal tension wave. The tension wave passes by the position of the stress wave sensors which detect the magnitude, sense and time of passage and communicate this information to the computer 46.

The longitudinal tension wave is then reflected from the impact end of the specimen and transformed into a longitudinal compressional wave. The process just described thereafter repeats a number of times with the magnitude of the moving stress wave decreasing with each passage of the wave by the sensors. The rate of decrease in the stress wave magnitude is the rate of attenuation which is used in the analysis described below to predict one or more mechanical properties of the specimen being tested. The information gathered from the stress wave sensors is also analyzed to determine the velocity of the stress wave as it moves through the specimen. The stress wave velocity is used in the indicated analysis to predict mechanical properties of the specimen as explained below.

The indicated analysis is based upon three factors which can be combined to reliably relate and predict mechanical strength and elastic properties of individual structural elements such as specimen 122. These factors are: the square of the wave speed through the material; the density or specific gravity of the material; and the rate of attenuation of the wave energy as it passes through the structural member.

It has been found that at least the strength in flexure or bending, the ultimate tensile strength, and the internal bonding strength can be reliably tested and predicted. It has also been found that the moduli of elasticity in bending and in tension can be reliably tested and predicted. Other mechanical strength and elastic properties may also be predictable.

The prediction of the indicated and possibly other mechanical properties is based upon the relationship expressed by Equation 1 below.

$$P = a \cdot D^x (ATT)^y (C^2)^z \qquad \text{Equation 1}$$

where
- $a$ = is a coefficient specific to the system, materials, and structural elements employed
- $D$ = the density or specific gravity
- $ATT$ = the rate of attenuation of the stress wave intensity
- $C$ = the wave speed through the material
- $x, y$ and $z$ = experimentally derived parameters specific to the system, materials, and structural elements used The attenuation rate (ATT) is typically defined as the average rate of attenuation of the stress wave. More specifically, it has been found represented as the average rate of particle velocity attenuation where velocity measurements are made of the particles forming the structural element. Attenuation in systems measuring wave dynamics by changed displacement and acceleration variations can also be used where appropriate interpretation is made in accordance with the physical theories of wave phenomenon.

The average rate of attenuation can advantageously be expressed as the percentage decline in particle maximum velocity per distance of travel through the member being tested. The attenuation rate is measured during testing using the stress wave sensor 145 and the known distances between the point of impact and the stress wave sensor. The rate of decrease or attenuation varies in relationship to the strength of the structural element being tested. The attenuation rate cannot, however, be used alone to provide a reliable indication of the indicated mechanical properties. The other measured quantities of wave speed and material density also are not by themselves reliable indicators of the mechanical properties of entire structural elements made from composite materials.

Testing machine 100 records the time of sensing of the propagating stress waves. The sensor location is known and the size of the specimen and distance through which the stress wave propagates within the specimen are also known. From the known spacial geometry and measured times of sensing of the stress wave, it is possible to determine the wave speed C. The measured wave speed, C, and measured attenuation rate, ATT, are then expressed into Equation 1 along with predetermined values for a, x, y, z and D.

The density, D, is measured by the optical scanner 180 and the weighing load cell 140 which measure size and weight data and communicate it to computer 46. Density is perferably measured during manufacturing to provide item-by-item specific measurements of density, thereby increasing accuracy of the process.

The predetermined values for a, x, y, and z are preferably determined by testing a population of similar structural elements and then destructively or otherwise determining the flexural, tensile, and internal bond breaking strengths or other mechanical properties using well-known destructive testing methods and apparatuses. When Equation 1 is used to predict elastic properties of the structural element such as the elastic moduli in bending or tension, then it is necessary to establish such predetermined parameters experimentally using accepted methods of determining the static or dynamic moduli of elasticity, well-known in the art. Experimental establishment of the predetermined parametric values for Equation 1 should be performed for each type of specimen and specific testing apparatus such as apparatus 100. The values for parameters a, x, y, and z should also be experimentally established for each type of structural element being analyzed and for each composition of nonhomogeneous or composite materials used in the structural element.

Experimental establishment of parameters a, x, y and z is advantageously accomplished using regression correlation techniques. In such techniques the measured strength or elasticity from experimental testing is correlated to the measured stress wave speed C, attenuation rate (ATT) and density D for the same specimens. A statistically significant number of specimens are used and an effective mathematical relationship is established which relates the destructive testing established values to the three measured variables of Equation 1. The regression technique correlates the experimental values and allows estimation of the predictive parameters a, x, y and z so that reliable prediction can be made of the mechanical properties using the measured variables C, ATT and D.

Computer 46 preferably includes analytical software for automatically calculating wave speed (C), density (D), and attenuation (ATT). Predetermined experimentally derived parameters a, x, y and z are used so that a predicted value of flexural or tensile strength, bond strength, flexural or tensile elastic moduli, or other properties can be predicted.

After the specimen has been tested in the testing position shown for specimen 122, the computer controls the specimen support actuator 135 causing them to retract and lower the specimen into a lowered position and onto the conveyor 120. The computer also controls the conveyor causing the tested specimen to move toward the left as shown in FIG. 1 to assume the marking position shown for specimen 123. The computer analysis of the specimen can be performed in less than a second and the grade status of the specimen determined while the specimen is lowered and moved to the marking position. The computer or process controller then controls the marker or markers 190 to extend the marking head or heads 193 into an extended marking position shown in phantom. The marking head advantageously inks or embosses a grade mark into the lumber or other specimen to permanently indicate the structural rating associated with the piece.

After the specimen has been marked, the process controller moves the conveyor 120 causing the tested and marked specimen to exit from the testing apparatus in any suitable fashion, such as by dropping onto an outflow conveyor, not shown, which would be to the right in FIG. 1. The outflow conveying system can be relatively simple or sufficiently complex to allow sorting of the outflowing lumber into different grading stockpiles.

Figure 3:
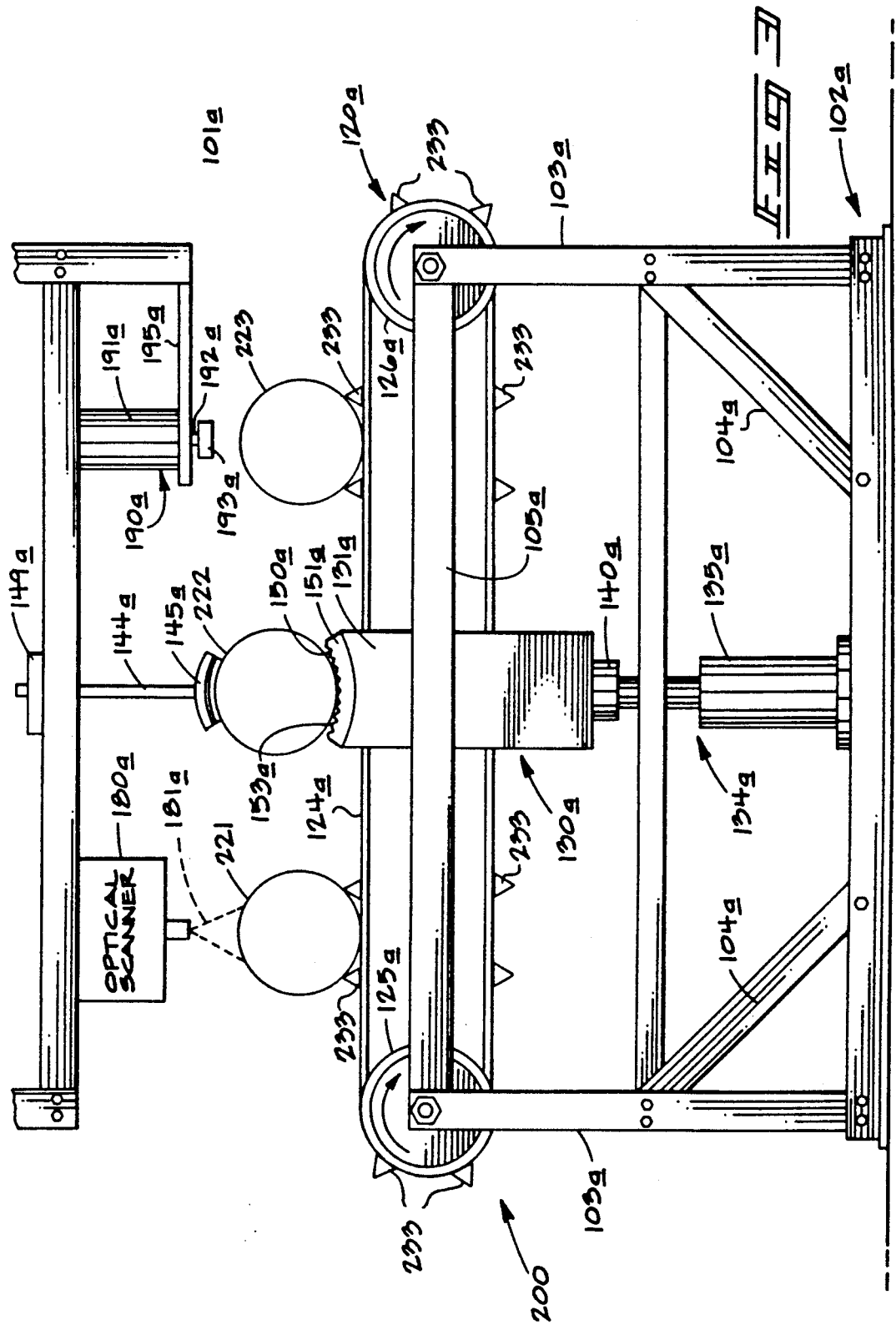
FIG. 3 is a front elevational view of another preferred testing apparatus according to this invention.
Figure 4:
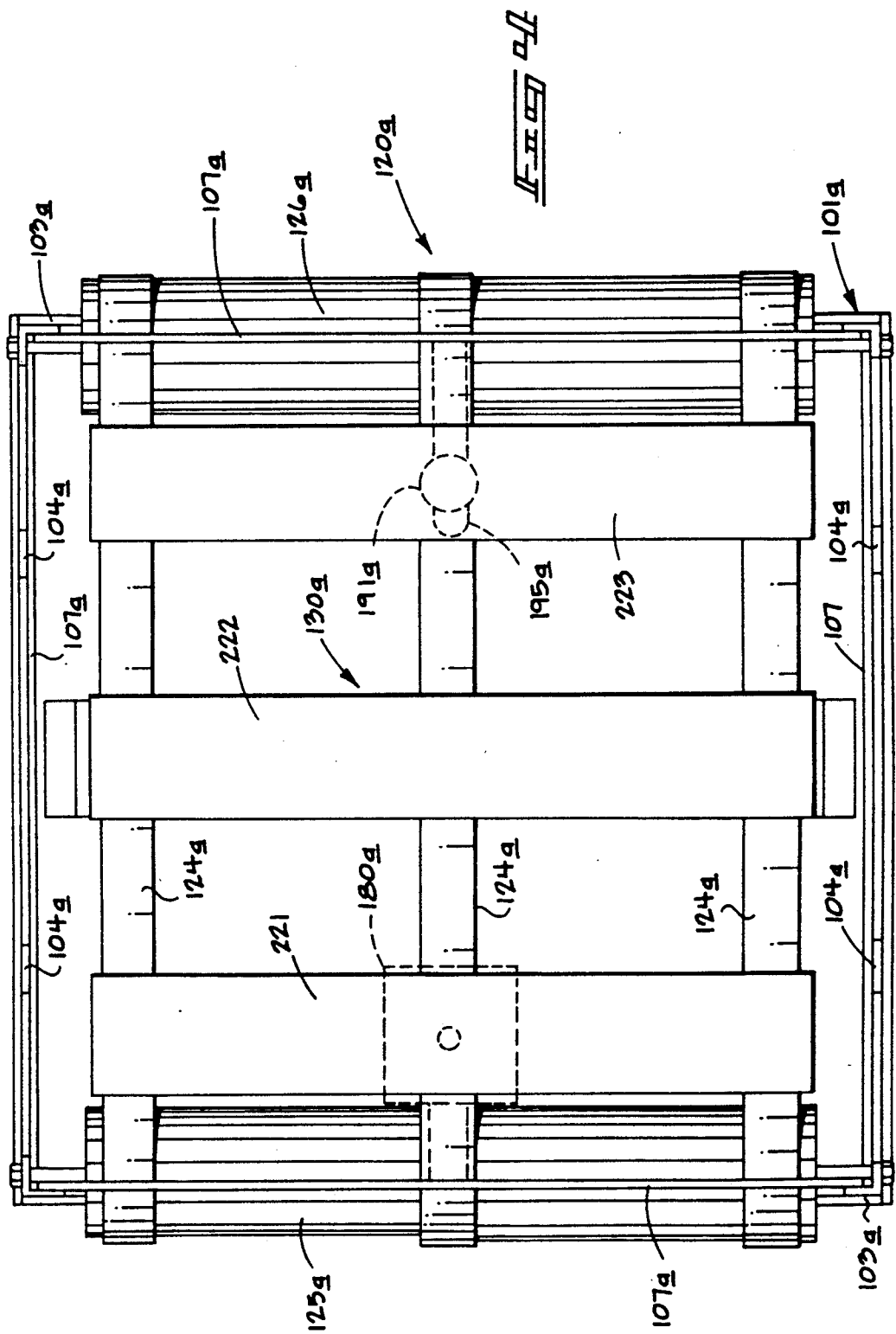
FIG. 4 is a top plan view of the embodiment shown in FIG. 3.

FIGS. 3 and 4 show another testing apparatus 200 which is substantially similar to testing apparatus 100 described above. Parts which are the same or similar are referenced with the same numeral as shown in FIG. 1 with an additional suffix "a". Parts which are different will be discussed below.

Testing apparatus 200 is specially adapted to test and predict the mechanical properties of wooden poles 221-223. To accomplish this the superstructure is supported by a building or other suitable support rather than using extended corner members 103 as shown in FIG. 1. The corner members 103a of apparatus 200 are below the elevation of the poles being supported on conveyor 120. This allows the relatively longer poles to extend outwardly from the testing apparatus and thereby allow various lengths of poles or other members to be tested.

The conveyor 120a of testing apparatus 200 is specifically adapted to hold poles 221-223 using chocks 233. The roughly cylindrical poles lay between adjacent chocks forming chock pairs. Other suitable means for conveying are alternatively possible.

The testing apparatus 200 also differs from apparatus 100 in that the specimen support surface 153a is concavely curved to cradle the nearly cylindrical shape of the specimen poles. The curved shaped can advantageously be provided by appropriately shaping the upper surfaces of the support extensions 131a. The specimen support layer 151a is also specially adapted to provide a stronger higher density resilient material, such as rubber, because of the greater weight of the poles 221-223 as compared to the smaller dimensional lumber specimens 121-123 for which testing apparatus 100 is adapted.

The testing apparatus 200 is preferably provided with an impactor subsystem as described above with reference to FIG. 10. The impactive projectiles are of greater mass and size than used in apparatus 100. In general the mass of the projectile is preferably in the range of 1:100 to 1:10,000 as compared to the mass of the specimen (mass of projectile:mass of specimen). More preferably the mass ratio is in the range 1:200 to 1:1,000. Results with ratios of approximately 1:400 have been particularly appropriate in testing boards of size 1 inch by 1 inch by 2 feet long.

The testing apparatus 200 has a stress wave sensor head 145a which is advantageously curved to provide more complete contact with the cylindrical poles being tested.

The testing apparatus 200 is preferably provided with a control system as provided in apparatus 100 and described above in connection with FIG. 9. The testing apparatus 200 operates automatically as described hereinabove for testing apparatus 100.

Figure 5:
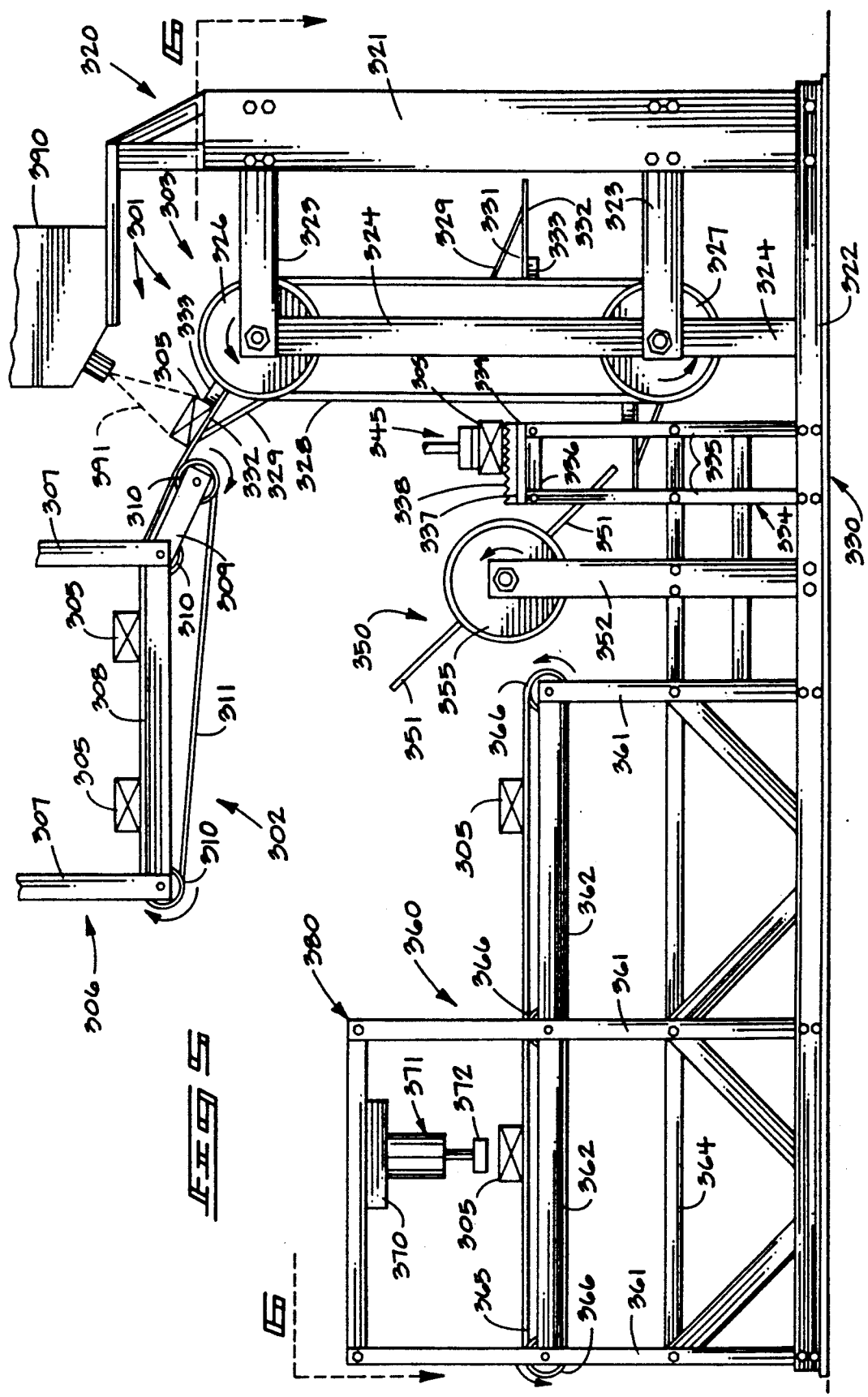
FIG. 5 is a front elevational view of further preferred testing apparatus according to this invention.
Figure 6:
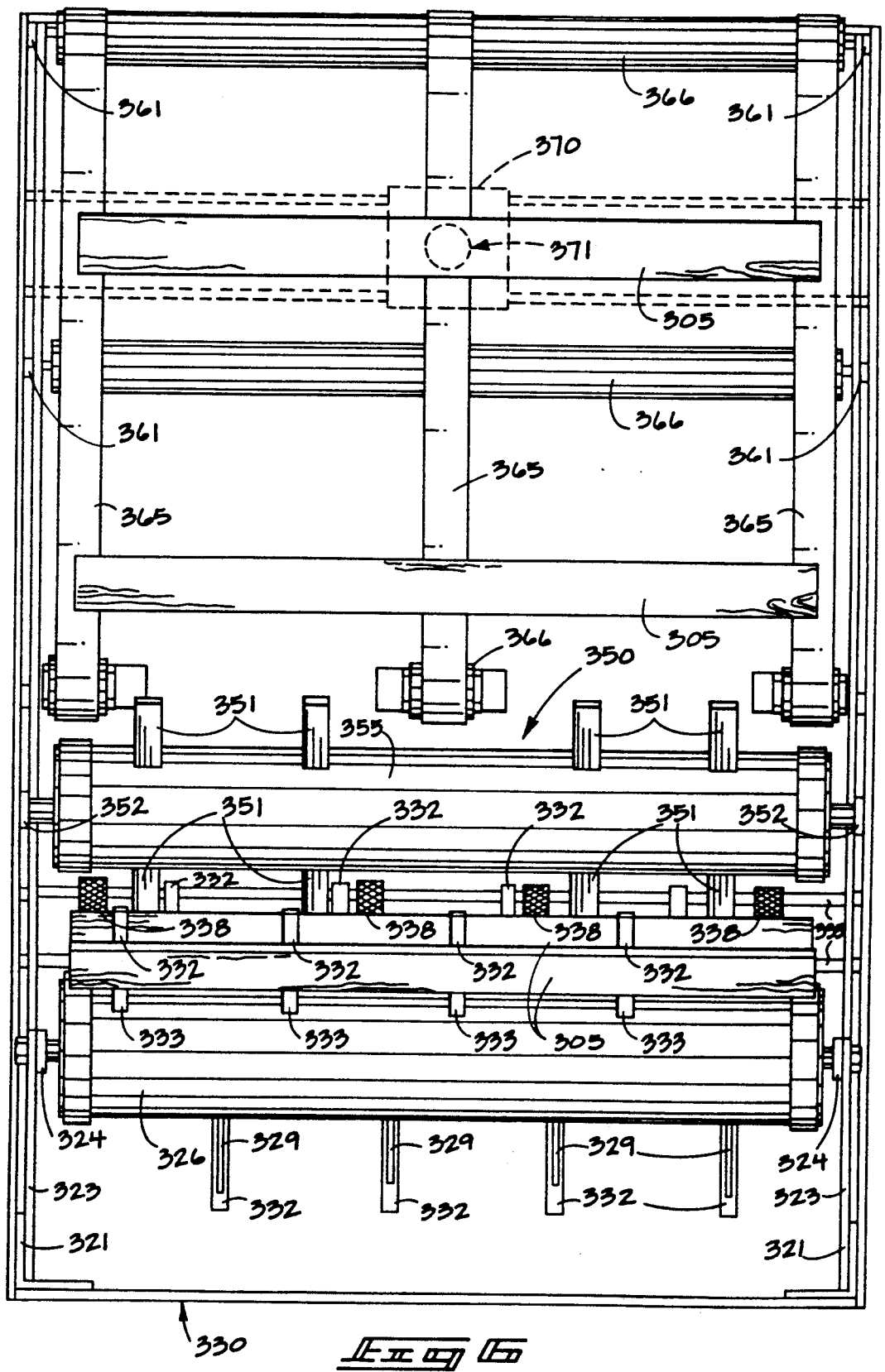
FIG. 6 is a top plan view of the embodiment shown in FIG. 5.

FIGS. 5 and 6 show a further alternative testing apparatus 300 in accordance with this invention. Testing apparatus 300 includes an infeed conveyor system 301 which includes a first infeed conveyor 302 and a second infeed conveyor 303. The first infeed conveyor 302 receives dimensional lumber pieces 305 from a related lumber feeding apparatus, not shown. The lumber pieces are advantageously fed into conveyor 302 in an endwise fashion. The first infeed conveyor includes a frame 306 which includes vertical hanger members 307 which are advantageously hung from the structural members of a building in which the testing apparatus is installed, or from other alternative structures. The first infeed conveyor frame 306 also includes horizontal side members 308 which extend between the vertical hangers 307. The horizontal side members 308 are provided with obliquely angled cantilevered support extensions 309. A plurality of conveyor support rollers 310 extend across between corresponding side assemblies of the infeed conveyor to serve as the support upon which one or more flexible conveyor belts 311 are trained. The first infeed conveyor moves the lumber specimens from left to right as shown in FIG. 5, delivering the specimens to the second infeed conveyor 303.

An optical scanner 390, such as described hereinabove with respect to FIG. 1 is advantageously positioned to scan a laser beam 391 over the incoming lumber specimen to gather information of the size and thickness of the specimens.

The second infeed conveyor 303 serves as an elevator conveyor which lowers the specimens 305 onto the testing stand 330. The second or elevator infeed conveyor 303 includes a structural frame 320 which includes a pair of major upright members 321 which are connected to the testing apparatus base 322. Each upright member 321 has a pair of outwardly extending support arms 323 which are connected to a vertical bar 324 which is supported upon the base 322. The complementary opposing upright assemblies formed by upright members 321, support arms 323, and bars 324 serve to support the upper elevator conveyor roller 326 and the lower elevator conveyor roller 327. The conveyor rollers 326 and 327 support endless circuitous conveyor belts 328 thereover. Each conveyor belt 328 has a plurality of lumber catch members 329 connected thereto for receiving the test specimens 305 thereon. The lumber catch members 329 include a cantilever bracket portion 331 with a lumber receiving surface 332. The lumber receiving surface is furnished with a spacer block 333 which spaces the lumber specimens outwardly from the conveyor to allow appropriate positioning upon the testing stand 330.

Lumber or other specimens lowered by elevator conveyor 320 are received upon the testing stand 330. Testing stand 330 includes a frame 334 having upright legs 335. A table member or members 336 are supported near the top of the upright legs 335. A load cell or other weighing means 339 is supported by the top 336 and provided to weigh the test specimen. A specimen support layer 337 is supported upon the weighing device to support the test specimen thereon. The specimen support layer is advantageously a resilient polymer resin foam material shaped to have a plurality of independent protrusions to form an undulating support surface 338 which is not resistant to shear stress developed in the member during transmission of a stress wave therein during testing as explained hereinabove.

The test specimen 305 is impacted with a projectile impactor as described above with respect to FIG. 10. Such impactor subsystem is not shown in FIG. 5.

The induced stress wave in the test specimen is sensed by a sensor head 345 similar to the sensor head 145 describe above. A suitable sensor mount (not shown) is used to controllably position and retract the sensor head 345.

The tested specimens are removed from the test stand in a suitable manner such as by the specimen removal rotor 350. Specimen removal rotor is controlled by the testing apparatus control system to rotate when the test specimen is to be removed. The removal rotor is mounted upon two upright frame members 352 at opposing ends of the rotor. The rotor assembly 350 includes a central rotor piece 355 which is rotatably supported upon the upright frame members 352. The rotor piece 355 includes an internal motor (not shown) which is controlled by the testing apparatus control system to rotate the rotor. The removal rotor further includes a pair of oppositely directed rotor removal arms 351 which pass through slots or breaks formed in the testing stand table to lift the tested specimens upwardly, toward the left, and onto the outflow conveyor 360. The outflow conveyor is preferably constructed in two or more portions to allow the removal arms to pass between the outflow conveyor portions to bring the lumber specimens to rest on the upper surface of the outflow conveyor.

Outflow conveyor 360 includes a framework 361 connected to testing apparatus frame base 322. The framework includes a plurality of post members 361 which are connected to base 322 and extend upwardly to horizontal side rail members 362. The frameworks 360 also advantageously include intermediate horizontal bars 364 for additional strength. The parallel endless conveyor belts 365 forming the outflow conveyor are each supported upon a set of conveyor support rollers 366. The conveyor belts are driven using any suitable means such as by motor and pulley (not shown) or by internal motors within the rollers 366. The top surfaces of conveyors 365 move from right to left as shown in FIG. 5. A specimen grade marker 370 is mounted upon a superstructure 380 of the frame. The grade marker 370 includes a pneumatic ram 371 and embossing head 372 for marking a grade indicator into the surface of the lumber specimens which have been tested. The conveyor 360 also serves to remove and transmit the tested specimens to further desired automated handling equipment (not shown).

The testing apparatus 300 can be controlled with a control system as described above in connection with FIG. 9 and the testing apparatus 100 and 200. Control output signals are provided for the first and second infeed conveyors, the removal rotor 350 and for the outflow conveyor 360. Other control functions are similar to or the same as described hereinabove.

The testing apparatus 300 functions in a manner similar to that described hereinabove in connection with the testing machines 100 and 200. Lumber is fed to the first infeed conveyor 302 with the specimens 305 received upon the upper surfaces of the conveyor belt 311. The first infeed conveyor is controlled to properly deliver a specimen when the second infeed conveyor 303 is positioned with a specimen support arm awaiting receipt of the specimen, as shown in FIG. 5. The optical scanner scans the specimen and determines its size and thickness and this information is sent to the controller or computer as described hereinabove. The second or elevator conveyor 320 lowers the test specimens into the testing position shown in FIG. 5. The impactor is then automatically controlled to impact the test specimen on the testing stand. The sensor 345 receives an indication of the multiple passages of the stress wave induced by the impact of the impacting projectile as the wave reflects within the specimen. The measured stress wave information provides an indication of stress wave speed and stress wave attenuation rate for the particular specimen being tested. The measured quantities of stress wave speed, stress wave attenuation and density of the specimen are compared against preprogrammed parameters, such as described above, to provide an estimate of one or more mechanical properties of the test specimen. The estimate is also advantageously used to determine a specified grade. The computer or controller then marks the specimen with the appropriate grade mark for the estimated mechanical property or properties determined.

Figure 7:
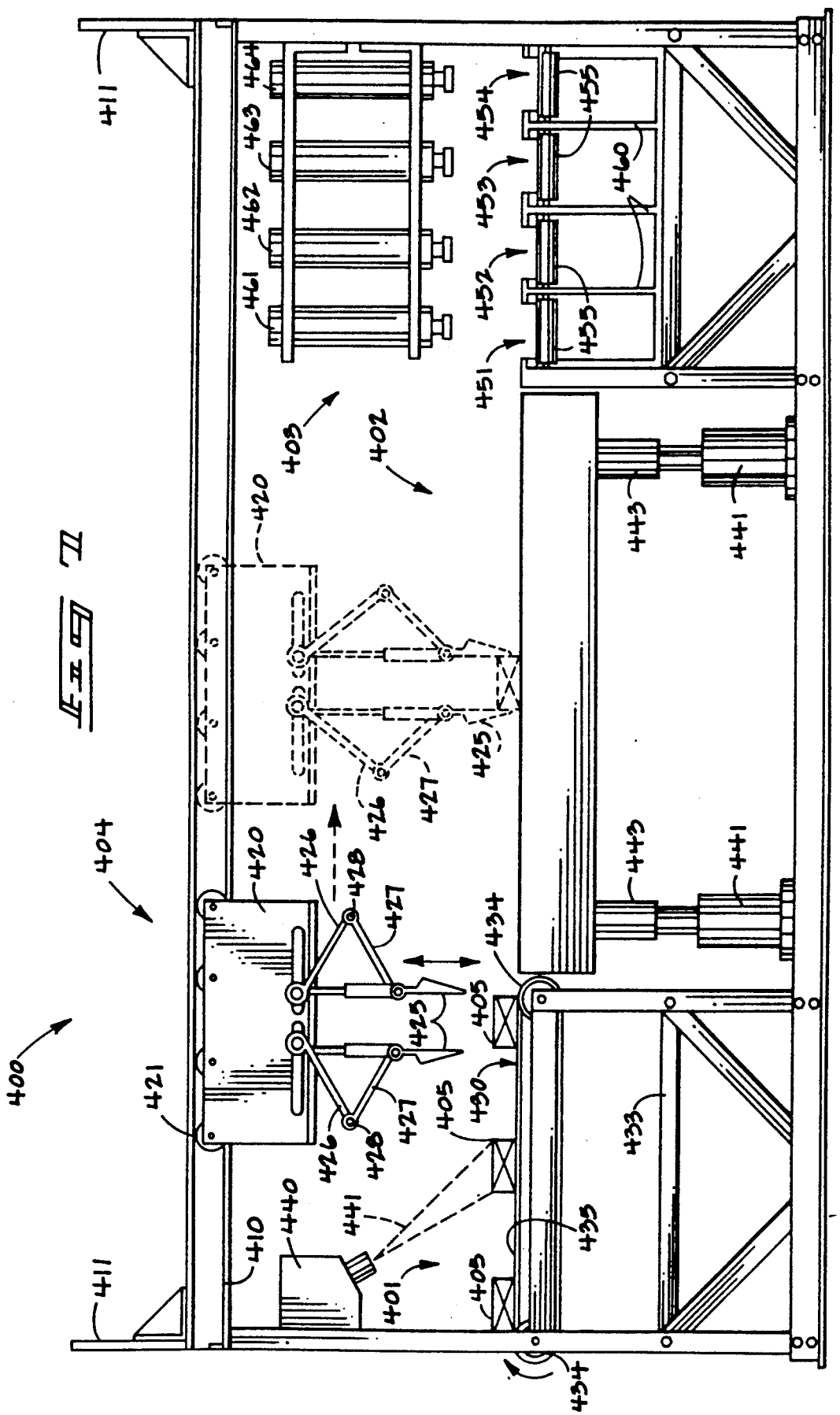
FIG. 7 is a front elevational view of a still further preferred testing apparatus according to this invention.
Figure 8:
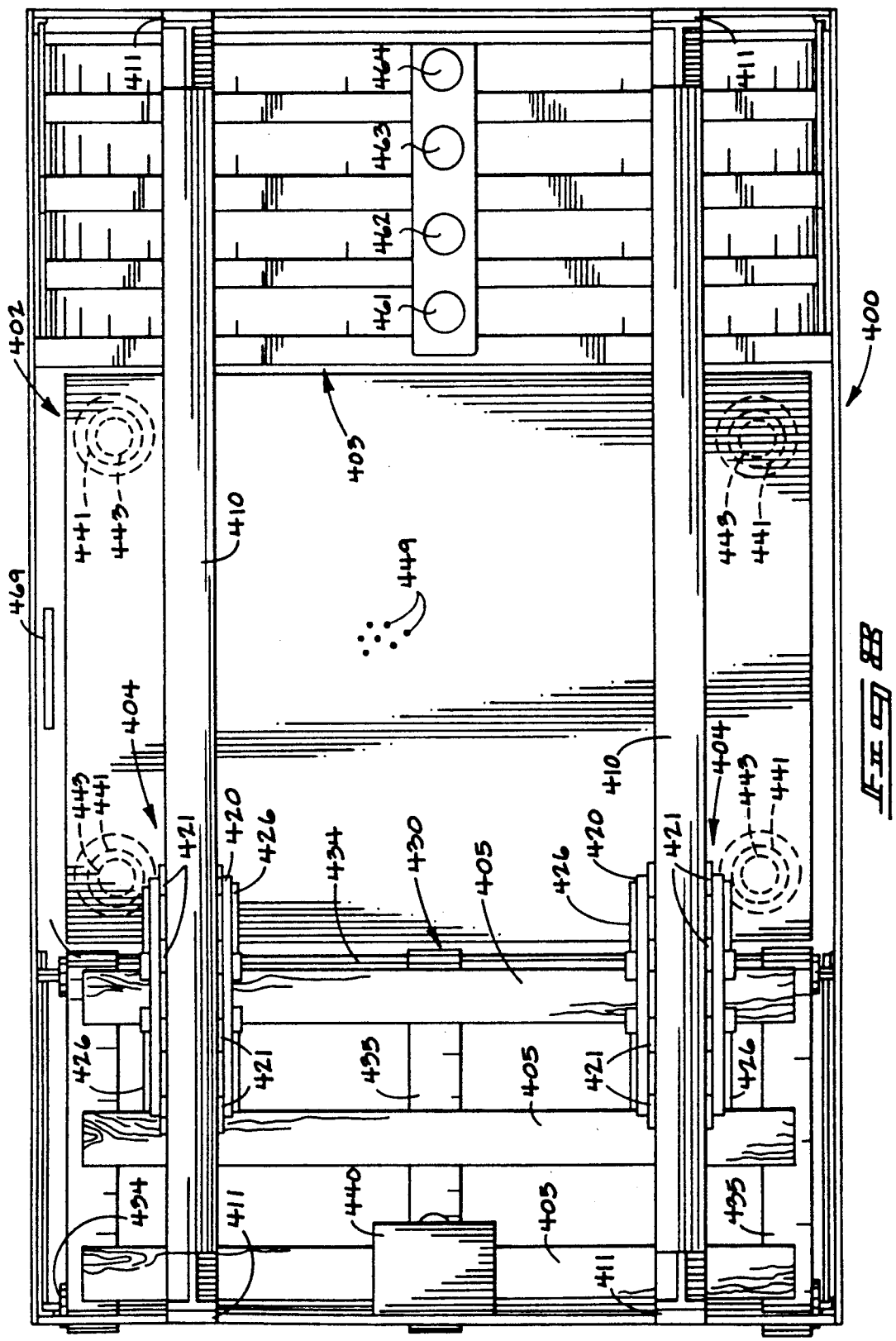
FIG. 8 is a top plan view of the embodiment shown in FIG. 7.

FIGS. 7 and 8 show a still further preferred testing apparatus 400 in accordance with this invention. Testing apparatus 400 includes an infeed table 401, testing stand 402, and outflow sorter 403. Testing apparatus 400 also includes an overhead specimen mover 404 which is used to move the specimens 405 to various positions in the process of testing and estimating the strength, elasticity or other mechanical property of the specimens. The overhead specimen mover includes a pair of overhead rails 410 which are suitably mounted to a frame or building structure such as by using mounting brackets 411. The rails 410 are adapted to allow translational motion of crane units 420 along the rails, left or right as shown in FIG. 7. The crane units move along the rails using crane wheels 421 which are either driven by a motor unit within the crane unit or a separate driver wheel can bear against the bottom of the rail and allow the crane unit to be moved along the rail. The crane unit also include two depending arms 423 which are mounted within the crane unit by hydraulic or pneumatic rams (not shown) to allow relative motion between the two so that specimens can be clamped between the jaws 425. The arm units 423 consist of upper and lower links 426 and 427 which are pivotally mounted together at a central joint 428. A hydraulic or pneumatic ram 429 extends between the upper end of link 426 and the lower end of link 427 to allow the jaws 425 to be moved up and down. This arrangement for the depending arms allow the specimens to be clamped and moved as desired along the testing apparatus. Other structures are alternatively possible.

The testing apparatus infeed table 401 advantageously includes a conveyor 430 for moving the test specimens 405 from left to right across the infeed table. The conveyor includes a framework 433 similar to those previously described herein which mount rollers 434 about which the conveyor belt 435 is trained. An optical scanner 440, such as described above, is mounted to scan a laser beam 441 at an oblique angle across and along the specimens to determine their particular size and thickness. The conveyor 430 allows the specimens to be clamped and picked for movement to the testing table 402.

Testing table 402 is supported upon legs 441 which are advantageously pneumatic cylinder and piston assemblies. At the upper end of the support legs 441 there are load cells 443 which produce an electronic signal indicative of the loading associated with the additional weight applied by the specimen being tested on the test table 402. The Test table is provided with a plurality of small holes 449 only a few of which are illustrated. The air hole 449 jet air upon which the weight of the test specimen is carried either totally or to a partial degree. The air support testing table is preferably partitioned inside to allow the area which actively jets air to be controlled dependent upon the size of materials which are being tested. This air cushion support system minimizes the attenuation of the stress wave which is caused by mechanical coupling between the test specimen and the support.

The impactor subsystem is as described above with respect to FIG. 10.

The stress wave sensor 469 used in testing apparatus 400 is shown in FIG. 8. The sensor is similar in description to sensor head 145. Sensor 469 also functions as a end stop against which the end of the specimen rests. Sufficiently coupling between the sensor and the end of the specimen is obtained by merely tilting the table toward the sensor 469.

The testing apparatus 400 also includes a sorter outflow conveyor 403 which includes a plurality of lanes 451–454. Each lane is provided with a number of specimen conveying rollers 455 which move the specimens into or out of the plane of the drawing as shown in FIG. 7. The rollers 455 are supported on the outflow conveyor frame 460 which can be constructed in a variety of arrangements suitable to the particular needs of the sorting apparatus. The rollers are driven by motors (not shown) which are controlled by the system controller as describe above with respect to FIG. 9.

Testing apparatus 400 is further advantageously provided with grade markers 461–464 for marking the appropriate indicator of grade or other mechanical property estimated using testing machine 400. The grade markers are extended downwardly by their supporting pneumatic rams to ink or emboss the surfaces of the lumber or other specimens thus indicating the grade or other property tested.

Testing apparatus 400 operates by receiving test specimens 405 from an associated piece of equipment (not shown). The incoming test specimens are moved by conveyor 430 to allow optical scanning by size scanner 440. The scanned specimens are then lifted by the overhead crane units 420 onto the testing table 402. Thereon the test specimen is supported at least partially by the jets of air emerging through the surface of the table. The weight of the specimen is sensed by the load cells 443 and the resulting weight information is communicated to the computer or system controller. The impactor strikes the end or the specimen causing a stress wave to be generated therein. The sensor 469 detects the passage, timing and amplitude of the stress wave as it reflects within the specimen. The information from the optical scanner and load cells is used to determine the density or specific gravity of the specimen being tested. The information gathered by the testing apparatus is compared against preprogrammed information which allows prediction of the mechanical properties based on these variables as explained hereinabove. The computer 46 produces an estimate of one or more mechanical properties based upon the sensed information and pre-programmed parameters. The resulting information is used to sort the specimens into the appropriate lane 451-454 associated with the particular specimen using the overhead crane units 420. The grade markers are similarly automatically controlled to mark the appropriate grade indicia on the tested specimens. The out flow sorter then conveys the tested, sorted specimens onto appropriate conveyors or other suitable equipment (not shown).

FIGS. 12 and 13 show an alternative preferred sensor assembly construction according to this invention. Sensor assembly 600 includes a mounting rod 644 which ends in a yoke 631. Yoke 631 is adapted to rotatable support the cylindrical sensor head 645 at pivots 632. The sensor head 645 includes a plastic backup cylinder 646 which is overlaid with a resilient layer 648. A thin layer 647 of piezoelectric film which actually senses the stress wave is mounted along the outer surface. The sensor layer has two electrodes at opposite ends of the piezoelectric strip forming which are connected through a commutator 670 to electrical wires 680 which carry the sensor signal to the computer or other elements of the control system as described above with respect to FIG. 9. The rotatable sensor assembly is advantageous in allowing a continuous stream of specimen boards 659 to be conveyed thereunder without necessarily being raised and lowered by an actuator.

The testing apparatus and methods of this invention are particularly adapted at testing relatively long or slender structural members. The ideal specimen are rod shaped, such as cylindrical or prismatic rods having a slenderness ratio in excess of 10:1. The slenderness ratio is the length divided by the maximum lateral dimension, such as diameter, or the greater of width or thickness. The stress waves induced in these members are preferably less than one quarter of the length of the specimen to provide superior testing performance.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. A method for automatically and nondestructively testing a structural member made of nonhomogeneous materials to quantitatively predict at least one mechanical property of the structural member, comprising:

automatically measuring the volume of the structural member to provide a structural member volume measure;

automatically weighing the structural member to provide a structural member weight measure;

automatically calculating density by dividing said structural member weight measure by said structural member volume measure to provide a structural member density measure which is indicative of the approximate density of the structural member;

automatically positioning the structural member into a testing position using a controlled positioning means;

supporting the structural member in said testing position in a manner which provides yieldable mechanical coupling with the structural member;

producing a moving stress wave within the structural member;

measuring a first intensity of the moving stress wave at a first point in time;

measuring a second intensity of the moving stress wave at a second point in time after said first point in time; said stress wave having traversed through the entire structural member at least once;

automatically calculating from said measuring steps to provide at least one stress wave attenuation rate which is indicative of the approximate rate at which said moving stress wave was attenuated as it traveled through the structural member during a travel period between at least said first and second points in time;

automatically calculating from said measuring steps to provide at least one stress wave velocity measure which is indicative of the approximate velocity of the moving stress wave as it moved through the structural member;

automatically calculating a predicted structural member mechanical property value using said structural member density measure, said at least one stress wave attenuation rate, and said at least one stress wave velocity measure, and predetermined and experimentally-derived parameters which correlate tested values of said mechanical property based upon measures of structural member density, stress wave attenuation, and stress wave velocity.

2. A method according to claim 1 and further defined by selecting the structural member to have a slenderness ratio in excess of 10.

3. A method according to claim 1 wherein said producing a moving stress wave produces within the structural member a longitudinal stress wave having a wavelength equal to less than one quarter a specimen length of the structural member.

4. A method according to claim 1 wherein said producing a moving stress wave includes impacting the structural member.

5. A method according to claim 1 wherein said producing a moving stress wave includes impacting the structural member with a projectile.

6. A method according to claim 1 and further comprising selectively grading the structural member based upon said predicted structural member mechanical property value.

7. A method according to claim 1 wherein said automatically calculating a predicted structural member mechanical property stimated value is further defined to be calculating flexural strength in bending.

8. A method according to claim 1 wherein said automatically calculating a predicted structural member mechanical property value is further defined to be calculating flexural elasticity.

9. A method according to claim 1 wherein said automatically calculating a predicted structural member mechanical property value is further defined to be calculating flexural modulus of elasticity.

10. A method according to claim 1 wherein said automatically calculating a predicted structural member mechanical property value is further defined to be calculating tensile strength.

11. A method according to claim 1 wherein said automatically calculating a predicted structural member mechanical property value is further defined to be calculating tensile elasticity.

12. A method according to claim 1 wherein said automatically calculating a predicted structural member mechanical property value is further defined to be calculating tensile modulus of elasticity.

13. A method according to claim 1 wherein said automatically calculating a predicted structural member mechanical property value is further defined to be calculating internal bonding strength.

14. A method according to claim 1 wherein said automatically positioning, said automatically weighing, and said supporting are performed by controllably and automatically lifting the structural member into the testing position using a structural member support assembly having a weighing means incorporated thereinto and at least one structural member support surface which is flexible and resilient.

15. A method according to claim 1 wherein said automatically measuring the volume of the structural member is performed by optically scanning the structural member to estimate the volume of the structural member.

16. A method according to claim 1 and further comprising automatically marking the structural member with an automated marking means to indicate said predicted structural member mechanical property value.

17. A method according to claim 1 wherein said automatically positioning and said automatically weighing are performed by controllably and automatically lifting the structural member into the testing position using a structural member support assembly having a weighing means incorporated thereinto.

18. An automatic non-destructive structural member testing apparatus for nondestructively testing and predicting at least one mechanical property of a structural member made from nonhomogeneous materials, comprising:
a frame;
at least one automatic control means;
at least one specimen positioning means supported by the frame and controlled by said automatic control means to controllably position the structural member relative to portions of the testing apparatus;
at least one structural member support controlled by said automatic control means for controllably supporting the structural member during testing thereof; said at least one structural member support having specimen support means which provide yieldable mechanical coupling with the structural member;
at least one stress wave inducer mounted for contact with the structural member for producing a moving stress wave in the structural member;
at least one stress wave sensor mounted for controlled detection of the structural member to detect a characteristic of the moving stress wave at a minimum of two different points in time;
automatic specimen weighing means for automatically weighing the structural member being tested to provide a structural member weight measure;
automatic specimen volume measuring means for automatically measuring the structural member to provide a structural member volume measure;
programmable computational means for analyzing stress wave information from said at least one stress wave sensor, said structural member weight measure from said automatic specimen weighing means, and said structural member volume measure from said automatic specimen volume measuring means, to determine information indicative of:
at least one stress wave velocity which approximates the speed of the moving stress wave in the structural member,
at least one stress wave attenuation rate which approximates the rate at which the moving stress wave attenuates as it moves through the structural member, and
at least one structural member density which approximates the density of the structural member;
said computational means further including means for calculating using said at least one stress wave velocity, said at least one stress wave attenuation rate, and said at least one structural member density, and experimentally-derived predetermined parameters which correlate tested values of at least one mechanical property as a function of stress wave attenuation rate, stress wave velocity, and structural member density to nondestructively derive a predicted estimate of said at least one mechanical property for said structural member.

19. A testing apparatus according to claim 18 and further comprising a structural member support actuator connected to said structural member support for controllably moving specimen contacting portions of the structural member support into engagement with the structural member to provide support to the structural member during testing.

20. A testing apparatus according to claim 18 and further comprising means for sorting tested structural members as a function of said predicted estimate of said at least one mechanical property.

21. A testing apparatus according to claim 18 wherein said at least one structural member support includes specimen contacting portions including a flexible layer which contacts the structural member during testing.

22. A testing apparatus according to claim 18 wherein said at least one structural member support includes specimen contacting portions having an undulating flexible layer which contacts the structural member during testing.

23. A testing apparatus according to claim 18 wherein said at least one structural member support includes specimen contacting portions having fluid apertures which apply fluid pressure to the structural member providing support to the structural member during testing.

24. A testing apparatus according to claim 18 wherein:
said at least one structural member support includes a structural member support actuator for controllably moving specimen contacting portions of the structural member support into engagement with the structural member to provide support to the structural member during testing; and
said automatic specimen weighing means is connected with the structural member support actuator to weigh the structural member when the structural member support actuator is operated to engage the structural member.

25. A testing apparatus according to claim 18 further comprising structural member feed machinery for feeding the structural member being tested to said testing apparatus.

26. A testing apparatus according to claim 18 further comprising structural member outflow machinery for removing the structural member being tested from said testing apparatus.

27. A testing apparatus according to claim 18 wherein said stress wave inducer is an impactor which is adapted to strike an end of the structural member to induce a longitudinal moving stress wave therein.

28. A testing apparatus according to claim 18 wherein said stress wave inducer is an elongated impactor which is adapted to strike and end of the structural member to induce a longitudinal moving stress wave therein.

29. A testing apparatus according to claim 18 wherein said stress wave inducer is an impactive projectile which is adapted to strike an end of the structural member to induce a longitudinal moving stress wave therein.

30. A testing apparatus according to claim 18 and further comprising:

structural member feed machinery for feeding the structural member being tested to said testing apparatus;

structural member outflow machinery for removing the structural member being tested from said testing apparatus.

31. A testing apparatus according to claim 18 and wherein the automatic specimen volume measuring means includes a scanning optical volume measuring means.

32. A testing apparatus according to claim 18 and further comprising a grade marker for automatically marking indicia on the structural member after testing which is indicative of said predicted estimate of said at least one mechanical property of the structural member.

* * * * *